(12) United States Patent
Holmberg et al.

(10) Patent No.: US 10,253,131 B2
(45) Date of Patent: Apr. 9, 2019

(54) POLYMERS PREPARED FROM FUNCTIONALIZED DIMETHOXYPHENOL MONOMERS

(71) Applicants: Angela L. Holmberg, Circle Pines, MN (US); Kaleigh H. Reno, Newark, DE (US); Thomas H. Epps, III, Bear, DE (US)

(72) Inventors: Angela L. Holmberg, Circle Pines, MN (US); Kaleigh H. Reno, Newark, DE (US); Thomas H. Epps, III, Bear, DE (US)

(73) Assignee: UNIVERSITY OF DELAWARE, Newark, DE (US)

(*) Notice: Subject to any disclaimer, the term of this patent is extended or adjusted under 35 U.S.C. 154(b) by 0 days.

(21) Appl. No.: 15/208,135

(22) Filed: Jul. 12, 2016

(65) Prior Publication Data

US 2017/0015775 A1    Jan. 19, 2017

Related U.S. Application Data

(60) Provisional application No. 62/191,551, filed on Jul. 13, 2015.

(51) Int. Cl.

| | |
|---|---|
| *C08F 12/22* | (2006.01) |
| *C08F 12/24* | (2006.01) |
| *C07C 39/19* | (2006.01) |
| *C07C 39/20* | (2006.01) |
| *C07C 63/04* | (2006.01) |
| *C07C 63/64* | (2006.01) |
| *C07C 49/794* | (2006.01) |
| *C08F 293/00* | (2006.01) |
| *C07C 69/54* | (2006.01) |

(52) U.S. Cl.
CPC .......... *C08F 293/005* (2013.01); *C07C 69/54* (2013.01); *C07C 39/19* (2013.01); *C07C 39/20* (2013.01); *C07C 49/794* (2013.01); *C07C 63/04* (2013.01); *C07C 63/64* (2013.01); *C08F 12/22* (2013.01); *C08F 12/24* (2013.01)

(58) Field of Classification Search
CPC .......... C08F 12/22; C08F 12/24; C07C 39/19; C07C 39/20; C07C 63/04; C07C 63/64; C07C 49/794
See application file for complete search history.

(56) References Cited

U.S. PATENT DOCUMENTS

| | | | | |
|---|---|---|---|---|
| 5,948,590 A | * | 9/1999 | Aoshima | G03F 7/0045 430/270.1 |
| 6,121,398 A | | 9/2000 | Wool | |
| 7,524,909 B2 | | 4/2009 | Palmese | |
| 2007/0269480 A1 | | 11/2007 | Richard | |
| 2012/0295993 A1 | | 11/2012 | Wool | |
| 2013/0337711 A1 | | 12/2013 | Wool | |
| 2014/0275435 A1 | | 9/2014 | Holmberg | |

FOREIGN PATENT DOCUMENTS

| | | | |
|---|---|---|---|
| JP | 10306145 A | * | 11/1998 |
| JP | 2006259558 A | * | 9/2006 |

OTHER PUBLICATIONS

Schraub, M. et al., "Selective [2+2]-Cycloaddition in Methacrylic Stilbene Polymers without Interference from E/Z-Isomerization". Macromolecules 2011, 44, 8755-8762.*
Kharas, G. B. et al., "Novel Copolymers of Styrene. 3. Oxy Ring-disubstituted 2-cyano-3-phenyl-2-propenamides". Journal of Macromolecular Science, Part A: Pure and Applied Chemistry (2013) 50, 575-580. (Year: 2013).*
Saha, S. et al. "Substituent Effects in ATRP of Polystyrene Brushes". Polymer Preprints (American Chemical Society, Division of Polymer Chemistry) 2007, 48(1), p. 783. Meeting 233, Mar. 25-29, 2007, Chicago, IL. Polymer Surfaces and Interfaces group. (Year: 2007).*
Lau, W. Y. et al. "Polymerization behavior of 2,6-dimethoxystyrene". Canadian Journal of Chemistry 1969, 47(11), 2057-2060. (Year: 1969).*
Holmberg et al., "RAFT Polymerization and Associated Reactivity Ratios of Methacrylate-Functionalized Mixed Bio-oil Constituents", Polym. Chem. 2015, 6(31), 5728-5739.
Holmberg et al., "Syringyl Methacrylate, a Hardware Lignin-Based Monomer for High Tg Polymeric Materials," ACS Macro Lett. 2016, 5, 574-578.
Moad et al., "Living Radical Polymerization by the RAFT Process." Aust. J. Chem., 2005, 58(6), 379-410.
AzkoNobel Product Data Sheet: Perkadox AIBN. AkzoNobel PolymerChemistry: Amersfoort, The Netherlands, 2015, 1-4.
J.A. Brydson et al., Plastics Materials, 1995, 8 pages.
Brian Douglas Mather "Non-Covalent Interactions in Block Copolymers Synthesized via Living Polymerization Techniques", 2007, 593 pages.
Christopher L. Lewis, "Structure Property Relationships for Polymers Bearing Reversibly Associating Side-groups", Department of Chemical Engineering, Arts, Sciences and Engineering, Edmund A. Hajim School of Engineering and Applied Sciences, 2015, 237 pages.
Lewis et al., "The influence of Hydrogen Bonding Side-Groups on Viscoelastic Behavior of Linear and Network Polymers", Macromolecules, 2014, vol. 47, pp. 729-740.
Glasser et al., "Derivatives of Lignin and Ligninlike Models with Acrylate Functionality", Chapter 41, ACS Symposium Series, 1989, pp. 515-522.
Rojo et al., "The preparation of high conversion polymeric systems containing eugenol residues and their rheological characterization", Journal of Material Science; Materials in Medicine, vol. 19, 2008, pp. 1467-1477.

(Continued)

*Primary Examiner* — Richard A Huhn
(74) *Attorney, Agent, or Firm* — RatnerPrestia

(57) ABSTRACT

Dimethoxyphenol-based monomers containing polymerizable functional groups such as [meth]acrylate groups are useful for the preparation of polymers, wherein one or more dimethoxyphenyl moieties are part of side chains pendant to the backbones of the polymers. The polymers thereby obtained may have different, improved properties, such as higher glass transition temperatures, thermal stability and solvent resistance, as compared to polymers based on other types of lignin-derived monomers.

8 Claims, No Drawings

(56) References Cited

OTHER PUBLICATIONS

Beach et al., "Properties of Thermosets Derived from Chemically Modified Triglycerides and Bio-Based Comonomers", Applied Science, 2013, vol. 3, pp. 684-693.
Stanzione et al., "Vanillin-Based Resin for Use in Composite Applications", Green Chemistry, 2012, vol. 14, pp. 2346-2352.
Stanzione et al., "Lignin Model Compounds as Bio-Based Reactive Diluents for Liquid Molding Resins", ChemSusChem, 2012, vol. 5, pp. 1291-1297.
Stanzione et al., "Lignin-Based Bio-Oil Mimic as Biobased Resin for Composite Applications", ACS Sustainable Chemistry Engineering, 2013, vol. 1, pp. 419-426.
Yamada et al., "Low Ceiling Temperature in Radical Polymerization of 2, 6-Dimethylphenyl Methacrylate", Journal of Macromolecular Science: part A—Chemistry, vol. 15, Issue 2, 1981, 3 pages (Abstract only).
Holmberg et al., "A Facile Method for Generating Designer Block Copolymers from Functionalized Lignin Model Compunds", ACS Sustainable Chemistry & Engineering, 2014, 5 pages.
Holmberg et al., "Softwood Lignin-Based Methacrylate Polymers with Tunable Thermal and Viscoelastic Properties", Macromolecules, 2016, 10 pages.
Altwicker, "The Chemistry of Stable Phenoxy Radicals", Chemical Reviews, vol. 67, No. 5, Sep. 25, 1967, pp. 475-531.

\* cited by examiner

POLYMERS PREPARED FROM FUNCTIONALIZED DIMETHOXYPHENOL MONOMERS

CROSS-REFERENCE TO RELATED APPLICATIONS

This application claims priority from U.S. Provisional Application No. 62/191,551, filed Jul. 13, 2015. The disclosure of the aforementioned application is incorporated herein by reference in its entirety for all purposes.

FIELD OF THE INVENTION

The present invention relates to polymerizable monomers derived from or based on dimethoxyphenols such as syringol, polymers prepared from such monomers, and methods of making such polymers.

DESCRIPTION OF THE RELATED ART

To address sustainability challenges associated with petrochemicals, researchers have exploited a plethora of renewable chemicals to generate biobased, cost-effective, and thermomechanically useful macromolecules. Lignin is one renewable resource that shows promise as a desirable alternative to petroleum feedstocks, largely due to its abundance as a byproduct of pulp and paper refining. Corresponding lignin-based bio-oils (e.g., the volatile fraction of pyrolyzed lignin) contain numerous aromatic compounds that structurally mimic common monomers (e.g., bisphenol A and styrene) for polymer applications. The exact structure and composition of a lignin-based bio-oil is highly variable, depending on the biomass resource, lignin type and depolymerization route, among other factors. In general, the native components of all lignin-based bio-oils include phenols and guaiacols (2-methoxyphenols), whereas the native components of angiosperm (hardwood, e.g., oak and maple trees) and graminaceous (grassy, e.g., switchgrass and corn stover) bio-oils also include syringols (2,6-dimethoxyphenols).

Biobased compounds increasingly are being incorporated into thermoplastic elastomers (TPEs), pressure-sensitive adhesives, composite binders, and drug delivery vehicles, each of which is a system that benefits from macromolecules prepared via controlled polymerization techniques. The synthesis methods, such as reversible addition-fragmentation chain-transfer (RAFT), anionic or atom-transfer radical polymerization, among others, are desirable for facilitating the generation of polymers (including block copolymers) with precise macromolecular characteristics through the control of kinetic parameters. For RAFT polymerizations, important parameters include the apparent propagation rate (which describes monomer-to-polymer conversion rates) and the apparent chain-transfer coefficient (which describes the consumption rate of chain-transfer agent and the conversion-dependent change in polymer density). Kinetic parameters that are consistent, in addition to controllable, also facilitate comparisons of polymer properties due to the ease with which macromolecules of matching end-groups, molecular weights and dispersities can be prepared.

For the above applications, properties that are among the most indicative of material practicality are the glass transition temperature ($T_g$), degradation temperature ($T_d$), and the zero-shear viscosity. The $T_g$ indicates that temperature at which a macromolecule transitions between glassy (solid-like) and rubbery (liquid-like) behavior, and the zero-shear viscosity describes how easily a material may deform at a given temperature. Polymers with a $T_g$ slightly above 100° C. are useful for boiling-water-stable plastics, and polymers with a $T_g$ well above 100° C. are useful for high-temperature applications (e.g., machine parts and asphalt components). In theory, one could access polymers having $T_g$'s anywhere from 100° C. to 200° C. via biobased monomers and controlled polymerizations. At present, however, there is a dearth of actual examples of high molecular weight macromolecules having glass transition temperatures in the range of from about 135 to about 190° C.

BRIEF SUMMARY OF THE INVENTION

Various exemplary aspects of the present invention may be summarized as follows:

Aspect 1: A polymerizable monomer, comprised of a phenyl ring, two methoxy groups substituted on the phenyl ring, and at least one substituent on the phenyl ring comprised of at least one polymerizable functional group other than a hydroxyl group.

Aspect 2: The polymerizable monomer of Aspect 1, wherein the substituent comprised of at least one polymerizable functional group is substituted at position 1 of the phenyl ring and the two methoxy groups are substituted at the 2 and 6 positions of the phenyl ring, the 2 and 3 positions of the phenyl ring, the 2 and 4 positions of the phenyl ring, the 3 and 4 positions of the phenyl ring, or the 3 and 5 positions of the phenyl ring.

Aspect 3: The polymerizable monomer of Aspect 1 or 2, having a structure corresponding to formula (I):

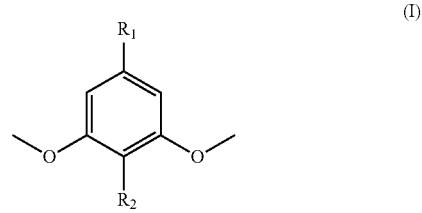

wherein $R_1$ is selected from the group consisting of hydrogen, hydroxyl, hydrocarbyl moieties and heteroatom-containing organic moieties; and wherein $R_2$ is the substituent comprised of at least one polymerizable functional group Aspect 4: The polymerizable monomer of Aspect 3, wherein $R_1$ is a hydrocarbyl group selected from the group consisting of alkyl groups, alkenyl groups, and allyl groups.

Aspect 5: The polymerizable monomer of Aspect 3 or 4, wherein $R_1$ is a heteroatom-containing organic moiety selected from the group consisting of aldehyde-containing groups, ketone-containing groups, carboxylic acid-containing groups, and hydroxyl-containing groups.

Aspect 6: The polymerizable monomer of any of Aspects 3 to 5, wherein $R_1$ is hydrogen, methyl, ethyl, n-propyl, i-propyl, formyl, acetyl, —CH$_2$C(=O)CH$_3$, —CH$_2$CH$_2$OH, —CH$_2$CH$_2$OH, —CH$_2$CHO, —CH$_2$CH$_2$CHO, —C(=O)CH$_2$CH$_3$, —CO$_2$H, —CH$_2$CO$_2$H, —C(=O)CH(OH)CH$_3$, —C(=O)CH(OCH$_2$CH$_3$)C(=O)CH$_3$, —CH(OCH$_2$CH$_3$)C(=O)CH$_3$, —CH=CHCHO, —CH=CHCH$_2$OH, —CH=CHCO$_2$H, —CH=CH$_2$, CH=CHCH$_3$ or —CH$_2$CH=CH$_2$.

Aspect 7: The polymerizable monomer of Aspect 3, wherein $R_1$ is hydrogen or formyl (—C(O)H).

Aspect 8: The polymerizable monomer of any of Aspects 1 to 7, wherein the at least one polymerizable functional group is an ethylenically unsaturated functional group.

Aspect 9: The polymerizable monomer of any of Aspects 1 to 8, wherein the at least one polymerizable functional group is selected from the group consisting of [meth] acrylate, maleinate, maleate, fumarate, [meth]acrylamide, vinyl, allyl, vinyl ester and vinyl amide.

Aspect 10: The polymerizable monomer of any of Aspects 3 to 6, wherein $R_2$ is [meth]acrylate.

Aspect 11: The polymerizable monomer of any of Aspects 3 to 6, wherein $R_1$ is hydrogen or formyl and $R_2$ is [meth] acrylate.

Aspect 12: A polymer comprising, in polymerized form, one or more polymerizable monomers in accordance with any of Aspects 1 to 11.

Aspect 13: The polymer of Aspect 12 additionally comprising, in polymerized form, one or more polymerizable co-monomers other than polymerizable monomers comprised of a phenyl ring, two methoxy groups substituted on the phenyl ring, and at least one substituent on the phenyl ring comprised of at least one polymerizable functional group other than a hydroxyl group.

Aspect 14: The polymer of Aspect 13, wherein the one or more polymerizable co-monomers are selected from the group consisting of lignin-based monomers, styrenes, phenyl [meth]acrylates, alkyl [meth]acrylates, [meth]acrylates other than alkyl [meth]acrylates and phenyl [meth]acrylates, terephthalates, amides, amines, diamides, diamines, dichlorides, nitriles, carboxylic acids, lactones, lactams, maleates, fumarates, malonates, maleinates, vinyls, vinyl esters, vinyl amides, [meth]acrylamides, thiols, dithiols, polythiols, enes, dienes, olefins, allyl monomers, azides, diazides, phosgene, carbonates, carbamates, succinates, alcohols, silanes, silicones, siloxanes, ethers, vinyl ethers, vinyl sulfides, isocyanates, epoxides, norbornenes, anhydrides and combinations thereof.

Aspect 15: The polymer of Aspect 13 or 14, wherein the polymer is a block copolymer, random copolymer, or gradient copolymer.

Aspect 16: A method of making a polymer, comprising polymerizing one or more polymerizable monomers in accordance with any of Aspects 1 to 11, optionally in combination with one or more polymerizable co-monomers other than polymerizable monomers in accordance with Aspect 1.

Aspect 17: The method of Aspect 16, wherein the polymerization is carried out using reversible addition-fragmentation chain transfer (RAFT) polymerization.

Aspect 18: A method of making a polymerizable monomer in accordance with any of Aspects 1 to 11, comprising reacting a dimethoxy-substituted phenol containing a phenolic hydroxyl group with a functionalized reagent containing at least one polymerizable functional group other than a hydroxyl group and at least one functional group reactive with the phenolic hydroxyl group.

Aspect 19: The method of Aspect 18, wherein the functionalized reagent is selected from the group consisting of anhydrides, acyl halides, alcohols, carboxylic acids, acrylamides, epoxies and vinyls and at least one functional group reactive with the phenolic hydroxyl group.

Aspect 20: The method of Aspect 18 or 19, wherein the polymerizable monomer is a dimethoxyphenol [meth]acrylate, the dimethoxy-substituted phenol is a syringol, a 2,3-dimethoxyphenol, a 2,4-dimethoxyphenol, a 3,4-dimethoxyphenol, or a 3,5-dimethoxyphenol and the functionalized reagent is [meth]acrylic anhydride or [meth]acryloyl chloride.

In various other aspects of the invention, syringyl methacrylate (also known as 2,6-dimethoxyphenyl methacrylate) is synthesized from syringol and subsequently polymerized using reversible addition-fragmentation chain-transfer polymerization. Homopolymers and heteropolymers (and copolymers) prepared from syringyl methacrylate and related monomers were found to have broadly tunable and highly controllable glass transitions temperatures ranging from 114° C. to 205° C. and zero-shear viscosities ranging from about 0.2 kPa·s to about 17,000 kPa·s at 220° C., with consistent thermal stabilities. The tailorability of these properties was found to be facilitated by the controlled polymerization kinetics of syringyl methacrylate, with the presence of two methoxy groups ortho to the methacrylate functionality surprisingly having a negligible effect on monomer reactivity (contrary to expectation). Syringol, the precursor to syringyl methacrylate, is an abundant component of depolymerized hardwood (e.g., oak) and graminaceous (e.g., switchgrass) lignins, making syringyl methacrylate and related syringol-based monomers a potentially sustainable and low-cost candidate for tailoring macromolecular properties.

The glass transition temperature for poly(syringyl methacrylate) was found to be greater than that reported in the literature for almost any other amorphous polymer lacking cyclic groups in its backbone, yet the monomer is readily polymerizable, especially in comparison to other high-$T_g$ phenyl methacrylates such as 2,6-dimethylphenyl methacrylate (structurally similar to syringyl methacrylate, but having methyl rather than methoxy groups at the 2 and 6 positions of the phenyl ring). Poly(syringyl methacrylate) was confirmed to have a $T_g$ approximately 120° C. higher than that of poly(2-methoxyphenol methacrylate); the introduction of a second o-methoxy group on the monomer thus results in a substantial increase in the glass transition temperature of the resulting homopolymer.

It was unexpected that thermally-stable syringol-based monomers could be obtained and successfully polymerized into useful macromolecules using the procedures described herein.

First, phenolic molecules with substituents at the 2- and 6-positions generally form stable radicals, dimers, and/or quinones, which make them either difficult to functionalize or radical scavengers (E. R. Altwicker, "The Chemistry of Stable Phenoxy Radicals," Chem. Rev., Vol. 67 (5), 1967, p. 475-531). These characteristics also make 2,6-difunctional phenols excellent polymerization inhibitors. Indeed, butylated hydroxytoluene (2,6-di-tert-butyl-4methylphenol) is a common antioxidant and additive used to prevent both polymer degradation and polymerization; a number of quinones, which can be easily prepared from syringols among other difunctional phenols, serve similar purposes.

Second, the most similar polymer known in the literature to the syringol-based polymers of the present invention could be considered to be poly(2,6-dimethylphenyl methacrylate), in which similarity is defined by the monomer being a sterically hindered (2,6-disubstituted phenyl) monomer. In one of the seminal works that studied the synthesis of this material (B. Yamada, S. Sugiyama, S. Mori, and T. Otsu, "Low Ceiling Temperature in Radical Polymerization of 2,6-Dimethylphenyl Methacrylate," J. Macromol. Sci. Chem., Vol. A15(2), 1981, p. 339-345), the authors found that the more sterically hindered the monomer, the more difficult it is to synthesize a polymer. Furthermore, the growing polymer would begin to depolymerize during synthesis if the temperature reached, for example, 73° C., and the thermal stability of the polymer was low in comparison to less-substituted phenyl methacrylates. As syringols themselves also are highly substituted (methoxy and methyl groups are both bulky), a skilled person would have likely assumed that the syringol-based monomers would behave similarly, either depolymerizing or degrading at low temperatures during or after synthesis, respectively. This would explain why, before now, neither syringol-based monomers nor other sterically hindered phenyl-based monomers (e.g., 2,6-di-tert-butylphenyl methacrylate) have been built into polymers. The examples included herein show that these assumptions are incorrect for syringol-based monomers. Indeed, the syringol-based monomers may be readily synthesized and may polymerize more rapidly than analogous less-substituted guaiacol-based monomers and the resulting polymers are just as thermally stable with higher glass transitions than the guaiacol-based polymer analogues.

DETAILED DESCRIPTION OF CERTAIN EMBODIMENTS OF THE INVENTION

The disclosure of the following article authored by the inventors, including the Supplemental Information associated therewith, is hereby incorporated by reference in its entirety for all purposes: Holmberg et al., "Syringyl Methacrylate, a Hardwood Lignin-Based Monomer for high $T_g$ Polymeric Materials," ACS Macro Lett. 2016, 5, 574-578.

As used herein, the term "dimethoxyphenol" refers to a phenol having two methoxy groups substituted on the aromatic ring, in addition to a hydroxyl group, wherein substituents (including hydrogen) are attached to the other carbon atoms of the aromatic ring. The methoxy groups may be substituted at various positions on the aromatic ring, such as the 2 and 3 positions, the 3 and 5 positions or the 2 and 6 positions (with the phenolic hydroxyl group being attached at the 1 position). As used herein, the term "syringol" refers to a 2,6-dimethoxyphenol with different moieties (including hydrogen) as substituents in the 4-position of the aromatic ring. A syringol thus corresponds to a compound having the following structure:

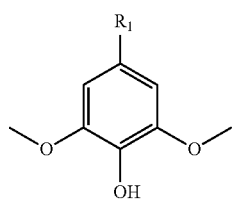

The p-position moiety ($R_1$) may be, for example, hydrogen (—H); alkyl groups (including linear, branched and cyclic alkyl groups, including C1-C6 alkyl groups such as methyl, ethyl, propyl, or butyl and isomers thereof); alkenyl and/or allyl groups (such vinyl, ethenyl, propenyl, butenyl); carbonyl-containing groups (especially aldehydes [formyl groups] and alkylformyl groups, acetyl and alkylacetyl groups, ketones and alkylketones, carboxylic acids and alkylcarboxylic acids, etc.); hydroxyl, hydroxyalkyl, or other alcohol-containing groups (e.g., hydroxyl, hydroxymethyl, hydroxyethyl, hydroxypropyl and the like); alkoxyl groups (e.g., methoxy, ethoxy, propoxy); and groups that contain combinations of different functional groups (e.g., ethoxy propenyl). Any of these moieties may be attached as substituents to the aromatic rings of other dimethoxyphenols within the scope of the present invention. The examples in the following Table 1 are the most commonly identified syringols that are currently known to exist in depolymerized lignin.

TABLE 1

| Names of Various "Syringols" | $R_1$ |
|---|---|
| syringol | H |
| 4-methyl syringol | $CH_3$ |
| 4-ethyl syringol | $CH_2CH_3$ |
| 4-propyl syringol | $CH_2CH_2CH_3$ |
| syringaldehyde | CHO |
| acetosyringone | $C=OCH_3$ |
| isopropiosyringone | $CH_2C=OCH_3$ |
| 4-(2-hydroxyethyl) syringol | $CH_2CH_2OH$ |
| 4-(3-hydroxypropyl) syringol | $CH_2CH_2CH_2OH$ |
| 2-syringyl-1-ethanal | $CH_2CHO$ |
| 3-syringyl-1-propanal | $CH_2CH_2CHO$ |
| 1-syringyl-1-propanone | $C=OCH_2CH_3$ |
| 1-syringyl-1,2-propanedione | $C=OC=OCH_3$ |
| syringic acid | COOH |
| 2-(4-hydroxy-3,5-dimethoxyphenyl) acetic acid | $CH_2COOH$ |
| 2-hydroxy-1-syringyl-1-propanone | $C=OC(OH)CH_3$ |
| 2-ethoxy-1-syringyl-1-propanone | $C=OC(OCH_2CH_3)CH_3$ |
| 1-ethoxy-1-syringyl-2-propanone | $CH(OCH_2CH_3)C=OCH_3$ |
| Sinapyl aldehyde | $CH=CHCHO$ |
| Sinapyl alcohol | $CH=CHCH_2OH$ |
| Sinapinic acid | $CH=CHCOOH$ |
| 4-vinyl syringol | $CH=CH_2$ |
| 4-propenyl syringol | $CH=CHCH_3$ |
| 4-allyl syringol | $CH_2CH=CH_2$ |

It is also possible and sometimes desirable to modify the native $R_1$ group and synthesize a new "syringol." These new synthetic syringols may include other moieties in the $R_1$ position including, but not limited to, alkyl (e.g., t-butyl), alkenyl, allyl, carbonyl, hydroxyl, hydroxyalkyl, or alkoxyl groups that are the same or different from those previously mentioned or amines, alkylamines, imines, alkylimines, acetals, hemiacetals, acrylamides, cyanates, cyanate acids, carboxyls, ethers, carbonyls, azides, cyanates, isocyanates, nitriles, thiols, dithioesters, thioesters, thiocarbonylthios, sulfides, disulfides, sulfates, sulfoxides, phosphoryls, esters, lactones (cyclic ester), lactams, epoxies, halides (chloride, bromide, fluoride, iodide), metallocenes, hydrazines, arylamines, anhydrides, diisocyanates, alkyl halides, acid chlorides, alkynes, sulfonamides, enols, enolates, enamines, saccharides, monosaccharides, nucleotides, and/or phospholipids that are not present in any syringol obtained directly from pyrolyzed lignin.

Generally, "syringols" are obtained from depolymerized hardwood lignins, in which the hardwood lignins come from biomass obtained from a plant such as, but are not limited to, oak, alder, chestnut, ash, aspen, balsa, beech, birch, boxwood, walnut, laurel, camphor, chestnut, cherry, dogwood, elm, eucalyptus, pear, hickory, ironwood, maple, olive, poplar, sassafras, rosewood, bamboo, coconut, locust, and willow trees, as well as, but not limited to, grasses (e.g., switchgrass, bamboo, straw), cereal crops (e.g., barley, millet, wheat), and agricultural residues (e.g., corn stover, bagasse). Syringol molecules also can come from petrochemical resources.

A "dimethoxyphenol-based monomer" in the context of the present invention is a dimethoxyphenol that has been modified to incorporate a moiety containing at least one polymerizable functionality (other than a hydroxyl group) at the phenol (—OH) position. Similarly, a "syringol-based monomer" in the context of the present invention is a syringol that has been modified to incorporate a moiety containing at least one polymerizable functionality (other than a hydroxyl group) at the phenol (—OH) position (the $R_2$ position), as shown in the following image (Formula (I)). Sometimes the term "syringyl" is used in place of "syringol" (as in "syringyl methacrylate", for example). The polymerizable functionality, in certain embodiments of the invention, is polymerizable through free radical mechanisms. In other embodiments, however, the polymerizable functionality is polymerizable through other mechanisms, such as anionic polymerization, cationic polymerization, condensation polymerization, ring-opening polymerization and so forth.

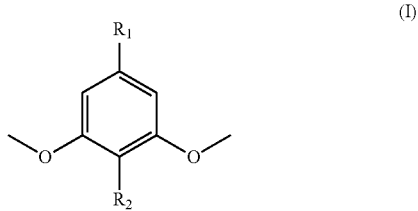

(I)

Polymerizable functionalities (e.g., for $R_2$) include, but are not limited to, ethylenically unsaturated functionalities such as methacrylate, acrylate, maleinate, maleate, fumarate, acrylamide, methacrylamide, vinyl, allyl, vinyl ester, and vinyl amide groups. These polymerizable groups can be attached to the "syringol" or dimethoxyphenol precursors using acylation or esterification reactions between the phenol (aromatic hydroxyl group) and a reactive moiety (i.e., a moiety reactive with the phenol) bearing at least one polymerizable group (e.g., $R_2$). Reagents that can provide the new polymerizable group include, but are not limited to, anhydrides (e.g., methacrylic anhydride, acrylic anhydride, maleic anhydride), acyl halides (e.g., methacryloyl chloride, acryloyl chloride, vinyl chloride, and bromide, iodine, or salt analogues thereof), alcohols (e.g., 2-hydroxyethyl methacrylate, 2-hydroxypropyl methacrylate, 2-hydroxyethyl acrylate, 2-hydroxypropyl methacrylate, etc.), carboxylic acids (e.g., methacrylic acid, acrylic acid, maleic acid), acrylamides (e.g., methacrylamide), epoxies (e.g., glycidyl methacrylate, glycidyl acrylate), and vinyls (e.g., vinyl chloride, vinyl bromide). Other polymerizable functionalities may include maleic, allyl, vinyl, hemiacetal, alkenyl, acetal, imine, amine, hydroxyl (provided that the monomer contains at least one additional polymerizable functional group other than a hydroxyl group), alkoxy, hydroxyalkyl, alkyl, alkenyl, acrylamide, cyanate ester, carboxyl, anhydride, ether, carbonyl, aldehyde, azide, cyanate, diisocyanate, isocyanate, nitrile, thiol, alkynyl, dithioesters, sulfide, sulfoxide, phosphoryl, disulfide, ester, cyclic ester, lactam (cyclic amide), sulfoxide, lactone (cyclic ester), or/and epoxy groups.

In one embodiment of the invention, a dimethoxyphenol-based monomer (e.g., a syringol-based monomer) is prepared by a method comprising reacting a dimethoxyphenol (e.g., a syringol) containing a phenolic hydroxyl group with a functionalized reagent containing at least one polymerizable functional group other than a hydroxyl group and at least one functional group reactive with the phenolic hydroxyl group. For example, the functionalized reagent may be selected from the group consisting of anhydrides, acyl halides, alcohols, carboxylic acids, acrylamides, epoxies, and vinyls. The polymerizable functional group may be selected from any of the above-mentioned polymerizable functionalities, particularly free radical-polymerizable functional groups, e.g., ethylenically unsaturated groups such as [meth]acrylates. The functional group reactive with the phenolic hydroxyl group may be selected, for example, from the group consisting of anhydride groups, acyl halide groups, epoxy groups, carboxylic acid groups, ester groups, vinyl halide groups and the like. Methacrylic anhydride, acrylic anhydride, and maleic anhydride are examples of particularly preferred functionalized reagents. A catalyst may be present to promote the desired reaction between the dimethoxyphenol/syringol and the functional group reactive with the phenolic hydroxyl group. For example, when the functionalized reagent is an anhydride, a tertiary amine may be utilized as a catalyst, typically at a concentration of from about 0.01 to about 0.1 mol/mol tertiary amine/anhydride. It may be advantageous to react the anhydride and the dimethoxyphenol (e.g., syringol) at an approximately 1:1 molar ratio or with the anhydride in a slight molar excess relative to the dimethoxyphenol (e.g., the molar ratio of anhydride:dimethoxyphenol is from about 1:1 to about 1.2:1). An inhibitor may be present during reaction of the dimethoxyphenol and the functionalized reagent, to stabilize the dimethoxyphenol-based monomer thereby formed and to reduce the extent of degradation or byproduct formation. Suitable inhibitors include, but are not limited to, sterically hindered alkylated phenols such as t-butyl-substituted phenols; typically, it will be desirable for about 500 ppm to about 3000 ppm of inhibitor to be present, based on the weight of the functionalized reagent. The reaction of dimethoxyphenol and functionalized reagent may be carried out in bulk or in an inert organic solvent such as toluene or tetrahydrofuran. The reaction temperature may be from about room temperature (25° C.) to about 100° C., for example. The reaction between the dimethoxyphenol and the functionalized reagent is allowed to proceed at the desired temperature for a time effective to achieve the desired degree of conversion of the starting materials to the dimethoxyphenol-based monomer (typically, about 1 hour to about 100 hours). The reaction product thereby obtained may then be worked up and purified using any of the techniques known in the field of organic chemistry, including washing a solution of the reaction product in a water immiscible organic solvent with one or more volumes of water (which may be neutral, acidic and/or basic), neutralization, concentration (removal of solvent, by distillation for example), fractionation, precipitation, (re)crystallization, distillation, chromatography and the like. It will generally be advantageous to purify the dimethoxyphenol-based monomer to a molar purity of at least 99% prior to utilizing the dimethoxyphenol-based monomer in a polymerization, although lower purities can be used if the impurity(ies) do(es) not negatively impact the desired polymerization.

In some cases, the functionalization procedure to attach the polymerizable functional group to the dimethoxyphenol may cause a chemical reaction to occur at one or more other substituents of the aromatic ring as well as at the phenolic —OH group. For example, functionalization of a "syringol" may cause a chemical reaction to occur at the $R_1$ position as well as at the phenolic —OH group. These reactions may make bifunctional, difunctional, or multifunctional monomers or change the structure of $R_1$ in addition to adding the polymerizable functionality as $R_2$. These types of reactions may result in $R_1$ containing methacrylate, acrylate, maleinate, maleate, fumarate, acrylamide, methacrylamide, vinyl ester, vinyl amide, maleic, allyl, vinyl, hemiacetal, alkenyl, acetal, imine, amine, hydroxyl, hydroxyalkyl, alkoxy, alkyl, alkenyl, alkynyl, acrylamide, cyanate ester, carboxyl, ether, carbonyl, aldehyde, azide, cyanate, isocyanate, diisocyanate, nitrile, thiol, dithioesters, sulfide, sulfoxide, phosphoryl disulfide, ester, lactone (cyclic ester), sulfoxide, lactam (cyclic amide), and/or epoxy groups that may be the same as, similar to, or different from the $R_1$ in the original "syringol" and the same as, similar to, or different from the new $R_2$ group. The difunctional, bifunctional, or multifunctional monomers can be used to make crosslinked materials and thermosets or graft and brush-like materials. Syringols and syringol-based monomers with modified $R_1$ groups provide an even greater range of properties than those accessible through syringols and syringol-based monomers with native $R_1$ groups.

As used herein, a dimethoxyphenol-based polymer refers to an oligomeric or macromolecular molecule comprised of at least one dimethoxyphenol-based monomer unit that has been polymerized at least by reaction of the polymerizable functional group(s) present in the monomer. Similarly, a syringol-based polymer as used herein refers to an oligomeric or macromolecular molecule comprised of at least one syringol-based monomer unit that has been polymerized minimally at the $R_2$ position (i.e., by reaction of the polymerizable functionality). The syringol-based monomer that comprises the syringol-based polymer also may have polymerized at the $R_1$ position in addition to the $R_2$ position. The homopolymerization of a syringol-based monomer corresponding to Formula (I) to provide a syringol-based polymer through reaction of a polymerizable functional group in $R_2$ may be schematically represented as follows (the substituent $R_1$, as previously mentioned, may also participate in the polymerization, if it contains a polymerizable functional group):

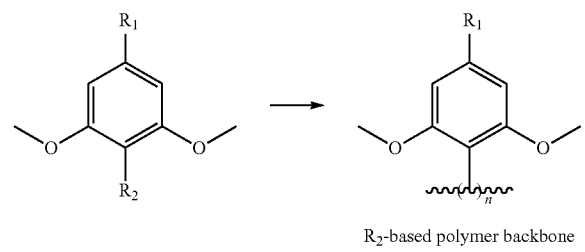

$R_2$-based polymer backbone

Dimethoxyphenol-based polymers in accordance with the present invention are not particularly limited with respect to their molecular weights or their geometry. For example, the dimethoxyphenol-based polymer may be either relatively low in molecular weight (oligomeric) or relatively high in molecular weight. The number average molecular weight of the dimethoxyphenol-based polymer may range from about 1000 daltons to about 5,000,000 daltons or even higher, for instance. The dispersity of the dimethoxyphenol-based polymer may be relatively low (e.g., less than 1.5, for example) or relatively high (e.g., 1.5 or greater). The dimethoxyphenol-based polymer may be, for example, linear, branched or even cross-linked in structure, depending upon the polymerization conditions, initiators and monomers used. If the dimethoxyphenol-based polymer is a copolymer or heteropolymer, the copolymer may be a block copolymer, a random (statistical) copolymer, gradient or tapered copolymer or the like. The dimethoxyphenol-based polymer may, in a preferred embodiment, be a thermoplastic, but may in another embodiment be a thermoset. The dimethoxyphenol-based monomers of the present invention also are useful in the preparation of thermoplastic elastomers, in particular thermoplastic elastomers which are block copolymers in which one or more blocks are blocks of one or more dimethoxyphenol-based monomers providing a "hard" polymerized segment having a relatively high $T_g$ (e.g., a $T_g$ of at least 100° C.) and one or more blocks are blocks of a monomer or mixture of monomers providing a "soft" polymerized segment having a relatively low $T_g$ (e.g., a $T_g$ of less than 0° C.).

Dimethoxyphenol-based polymers in accordance with the present invention may be synthesized by any number of polymerization techniques including, but not limited to, free-radical polymerization, reversible addition-fragmentation chain-transfer (RAFT) polymerization, ring-opening [metathesis] polymerization (RO[M]P), step-growth polymerization, cationic polymerization, anionic polymerization, coordination polymerization, condensation polymerization, emulsion polymerization, Ziegler-Natta polymerization, metallocene polymerization, group-transfer polymerization, living radical polymerization, reversible-deactivation radical polymerization, atom-transfer radical polymerization (ATRP), stable free radical polymerization (SFRP), TEMPO polymerization, cobalt-mediated radical polymerization, nitroxide mediated radical polymerization (NMP), catalytic chain-transfer polymerization, iniferter polymerization, iodine-transfer polymerization (ITP), selenium-centered radical-mediated polymerization, telluride-mediated polymerization, stibine-mediated polymerization, cationic ring-opening polymerization, and/or catalyst-transfer polycondensation.

In a particular preferred embodiment, reversible addition-fragmentation chain-transfer (RAFT) polymerization is employed to prepare a dimethoxyphenol-based polymer in accordance with the present invention. A dimethoxyphenol-based polymer may be prepared by a method comprising polymerizing at least one dimethoxyphenol-based monomer via reversible addition-fragmentation chain-transfer polymerization (RAFT), in the presence of a free radical initiator and a chain transfer agent, to form the dimethoxyphenol-based polymer. One or more co-monomers may optionally also be polymerized, either together as a mixture with the dimethoxyphenol-based monomer(s) or separately (sequentially or step-wise). Reversible Addition-Fragmentation chain Transfer or RAFT polymerization is one of several kinds of reversible-deactivation radical polymerizations. It makes use of a chain transfer agent, such as a thiocarbonyl-thio compound (e.g., a dithioester, a thiocarbamate or a xanthate, such as 2-cyano-2-propyl benzodithioate), to afford control over the generated molecular weight and polydispersity during a free-radical polymerization. The chain transfer agent mediates the polymerization of the dimethoxyphenol-based monomer(s) and optional co-monomers via a reversible chain-transfer process. The free radical initiator may be, for example, an azo compound such as 2,2'-azobisisobutyronitrile (AIBN) or 4,4'-azobis(4-cyanovaleric acid) (ACVA). The polymerization may be carried out in an organic solvent or mixture of organic solvents, such as anisole, typically at temperatures of from about 40° C. to about 120° C., or alternatively with no solvent (bulk). The polymerization also can be carried out as an emulsion-type polymerization wherein one or more emulsification agents and a solvent (e.g., water) are used. Typical for RAFT polymerizations, 0.02 to 0.4 moles of initiator may be used for each mole of chain transfer agent; the moles of chain transfer agent relative to the number of monomer(s) depends upon the target molecular weight and the monomer-to-polymer conversion. As with other controlled radical polymerization techniques, RAFT polymerizations can be performed with conditions to favor low dispersity (narrow molecular weight distribution) and a pre-chosen molecular weight. RAFT polymerization can be used to design polymers of complex architectures, such as linear block copolymers, comb-like, star, brush polymers, dendrimers and cross-linked networks.

The dimethoxyphenol-based polymer may comprise polymerized units of either a single chemically distinct dimethoxyphenol-based monomer (i.e., a homopolymer), a mixture of chemically distinct dimethoxyphenol-based monomers (to provide a copolymer), a mixture of one or more dimethoxyphenol-based monomers and one or more other lignin-based monomers such as guaiacol-based monomers (to provide a copolymer), or a mixture of one or more dimethoxyphenol-based monomers and one or more of any other type of polymerizable monomer (to provide a copolymer). Possible comonomers are those that can react under the same polymerization conditions as the dimethoxyphenol-based monomer(s). Such comonomers include, but are not limited to:

a). other lignin-based monomers (2-methoxyphenol and phenol derivatives with varying 4-position moieties) with similar structures and functionalities as the dimethoxyphenol-based monomers;

b). styrenes (styrene, 4-bromostyrene, 4-fluorostyrene, etc.); alkylstyrenes (4-methylstyrene, 2-methylstyrene, 2,4-dimethylstyrene, 4-ethylstyrene, benzhydrylstyrene, etc.);

c). phenyl [meth]acrylates with any number and position of substituents and especially those also derived or obtained from lignin (e.g., phenyl [meth]acrylate, 2-methylphenyl [meth]acrylate, 4-ethylphenyl [meth]acrylate, 4-methylphenyl [meth]acrylate, 4-propylphenyl [meth]acrylate, guaiacol [meth]acrylate, creosol [meth]acrylate, 4-ethylphenyl [meth]acrylate, 4-propylguaiacyl [meth]acrylate, eugenol [meth]acrylate, vanillin [meth]acrylate, trimethoxysilylpropyl [meth]acrylate, and the like);

d). alkyl [meth]acrylates with alkyl chain lengths anywhere from 1 to 36 carbon atoms and any number of unsaturated bonds and especially those that are derived or obtained from biobased resources (e.g., methyl [meth]acrylate, ethyl [methyl]acrylate, propyl [meth]acrylate, butyl [meth]acrylate, lauryl [meth]acrylate, palmitic [meth]acrylate, stearic [meth]acrylate, oleic [meth]acrylate, linoleic [meth]acrylate, and the like);

e). other types of [meth]acrylates (e.g., [meth]acrylic acid, perfluorooctyl [meth]acrylates, hydroxymethyl [meth]acrylate, hydroxyethyl [meth]acrylates, poly(oligo-ethylene glycol) [meth]acrylate, 3-sulfopropyl [meth]acrylate potassium salt, and the like);

f). terephthalates (e.g., polyethylene terephthalate, dimethyl terephthalate, butylene terephthalate, trimethylene terephthalate, dioctyl terephthalate, cyclohexylenedimethylene terephthalate, terephthalic acid, terephthaloyl chloride, and the like);

g). amides, amines, diamides, and diamines (e.g., hexamethylenediamine, diaminohexane, ethylenediamine, paraphenylenediamine, 4,4'-oxydianiline, putrescine, tetramethylene diamine, 2-methylpentamethylene diamine, trimethyl hexamethylene diamine, xylylene diamine, 1,5-pentadiamine, 11-aminoundecanoic acid, aminolauric acid, bis[para-aminocyclohexyl] methane, diethyltoluenediamine, dimethylthiotoluenediamine, triethanolamine, and the like);

h). dichlorides (e.g., hexanedioyl dichloride);

i). nitriles (e.g., acrylonitrile, 2-propenenitrile, methacrylonitrile, 2,6-dichlorobenzonitrile, pentachlorobenzonitrile);

j). carboxylic acids, including monocarboxylic acids, dicarboxylic acids and polycarboxylic acids (e.g., adipic acid, sebacic acid, terephthalic acid, isophthalic acid, dodecanedoic acid, 4-hydroxybenzoic acid, 6-hydroxynaphthalene-2-carboxylic acid, and the like);

k). lactones and lactone analogues (e.g., acetolactone, propiolactone, butyrolactone, valerolactone, caprolactone, dodecalactone, butenolide, macrolide, cardenolide, bufadienolide, lactide, cyclopentadenolide, coumarin, carvomenthide, menthide, tulipalin A, and the like), l). lactams (e.g., caprolactam, laurolactam, vinylcaprolactam, and the like);

m). maleates, malonates, and maleinates (e.g., dioctyl maleate, maleic acid, dimethyl maleate, maleic anhydride, diallyl maleate, diethyl allylmalonate) and associated isomers, such as fumarates;

n). vinyls (e.g., vinyl chloride, vinyl bromide, vinyl fluoride, 4-vinyl-styrene, ethylene, vinyl acetylene, vinyl naphthalene, vinylpyridine, vinylformamide, and the like);

o). vinyl esters (e.g., vinyl acetate, vinyl benzoate, vinyl 4-tert-butylbenzoate, vinyl chloroformate, vinyl cinnamate, vinyl decanoate, vinyl nenodecanoate, vinyl nenononanoate, vinyl pivalate, vinyl propionate, vinyl stearate, vinyl trifluoroacetate, vinyl valerate, and the like);

p). vinyl amides (e.g., N-methyl-N-vinylacetamide, vinylformamide, vinylacetoamide, vinyl amide, and the like);

q). [meth]acrylamides (e.g., alkyl [meth]acrylamides, butyl [meth]acrylamide, diacetone [meth]acrylamide, diethyl [meth]acrylamide, diethyl [meth]acrylamide, ethyl [meth]acrylamide, hexamethylenebis[meth]acrylamide, hydroxymethy[meth]acrylamide, hydroxyethyl [meth]acrylamide, isobutoxymethyl [meth]acrylamide, isopropyl [meth]acrylamide, [meth]acrylamide, phenyl [meth]acrylamide, triphenylmethyl [meth]acrylamide, and the like);

r). thiols, dithiols, and polythiols (e.g., butanedithiol, benzenedithiol, biphenyldithiol, benzenetrithiol, decanedithiol, dithiothreitol, dithioerythritol, dimercaptonaphthalene, ethanedithiol, hexanedithiol, octanedithiol, propanedithiol, pentanedithiol, thiobisbenzenethiol, and the like);

s). enes, dienes, and olefins (e.g., terpenes, sesquiterpenes, ethylene, propene, butylene, isoprene, acetylene, myrcene, humulene, caryophyllene, farnesene, limonene, methylpentene, ethylene, propylene, butadiene, decalene, tetrafluoroethylene, hexafluoropropylene, pinene, chloroprene, acetylene, and the like);

t). allyl monomers (e.g., allyl acetate, allyl acetoacetate, allyl alcohol, allylamine hydrochloride, allyl benzyl ether, allyl 2-bromo-2-methylpropionate, allyl butyl ether, allyl chloroacetate, allyl cyanide, allyl cyanoacetate, allyl ether, allyl ethyl ether, allyl methyl carbonate, allyl methyl sulfone, allyloxybenzaldehyde, allyloxyethanol, allyoxy propanediol, allyl phenyl ether, allylphosphonic acid monoammonium salt, allyl trifuloroacetate, tert-butyl allyl carbamate, butyne, diallyl carbonate, methylsulfonyl propyne, propyne, trimethylolpropane [di]allyl ether, and the like, including the [meth]allyl analogues thereof);

u). azides and diazides (ethynylene diazide, glycidyl azide, etc.);

v). phosgene;

w). carbonates, including cyclic carbonates;

x). carbamates;

y). succinates;

z). alcohols, including diols and polyols (e.g., 4-amino-4-3-hydroxypropyl-1,7-heptanediol, benzenedimethanol, biphenyldimethanol, bis-hydroxymethyl-butyric acid, dihydrobenzoic acid, propanediol, cyclohexanediol, cyclopentanediol, dihydroxybenzophenone, dihydroxyacetophenone, dihydroxynaphthalene, butanediol, catechol, hexanediol, hexanetriol, hydrobenzoin, hydroquinone bis-2-hydroxyethyl ether, 2-hydroxymethyl-1,3-propanediol, pentanediol, phenyl-1,2-propanediol, ethylene glycol, pentaerythritol, glycerol, trimethylolpropane, and the like);

aa). silanes, silicones, and siloxanes (e.g., dimethyldichlorosilane, silatrane glycol, tetramethyl-tetravinylcyclotetrasiloxane, and the like);

bb). ethers and vinyl ethers (e.g., vinyl ether, [di]glycidyl ether, butanediol [di]vinyl ether, butyl vinyl ether, chlorethyl vinyl ether, cyclohexyl vinyl ether, dodecyl vinyl ether, diethyl vinyl orthoformate, diethylene glycol [di] vinyl ether, phenyl vinyl ether, propyl vinyl ether, isobutyl vinyl ether, ethyl vinyl ether, ethylhexyl vinyl ether, ethylene glycol vinyl ether, and the like);

cc). vinyl sulfides (e.g., vinyl sulfide, phenyl vinyl sulfide, 4-chlorophenyl vinyl sulfide, bromphenyl vinyl sulfide, ethyl vinyl sulfide, and the like);

dd). isocyanates, including diisocyanates and polyisocyanates (e.g., diisocyanatobutane, diisocyanatododecane, diisocyanatooctane, hexamethylene diisocyanate, cyclohexylene diisocyanate, phenylene diisocyanate, tolylene diisocyanate, toluene diisocyanate, methylene diphenyl diisocyanate, isophorone diisocyanate, and the like);

ee). epoxides (e.g., ethylene oxide, allyl glycidyl ether, butadiene diepoxide, butanediol diglycidyl ether, butyl glycidyl ether, tert-butyl glycidyl ether, chlorophenyl glycidyl ether, cyclohexene oxide, cyclopentene oxide, dicyclopetadiene dioxide, dieldrin, diepoxycyclooctane, diepoxyoctane, N,N-diglycidyl-4-glycidyloxyaniline, epoxybutane, epoxybutene, epoxydodecane, epoxyhexane, epoxyhexene, epoxynorbornane, epoxyoctane, epoxypentane, epoxy-phenoxypropane, epoxypropyl benzene, epoxypropyl phthalimide, epoxytetradecane, ethylhexyl glycidyl ether, furfuryl glycidyl ether, glycidyl 4-methoxyphenyl ether, glycidyl methylphenyl ether, methyl vinyloxirane, pinene oxide, propylene oxide, resorcinol diglycidyl ether, stilbene oxide, styrene oxide, and the like);

ff). norbornenes (e.g., dicyclopentadiene, norbornene, bicycloheptadiene, and the like); and gg). anhydrides (e.g., [meth]acrylic anhydride, maleic anhydride, citraconic anhydride, crotonic anhydride, itaconic anhydride, methylglutaric anhydride, methylphthalic anhydride, methylsuccinic anhydride, naphthalic anhydride, phenylglutaric anhydride, phenylmaleic anhydride, and the like);

as well as combinations or mixtures of any two or more of the above-mentioned co-monomers.

The dimethoxyphenol-based polymer may be comprised, in various embodiments of the invention, of at least 1%, at least 5%, at least 10%, at least 20%, at least 30%, at least 40%, at least 50%, at least 60%, at least 70%, at least 80%, at least 90%, at least 95%, or at least 99% by weight or 100% by weight of dimethoxyphenol-based monomer(s) in polymerized form. The balance of the dimethoxyphenol-based polymer may be comprised of one or more of the above-mentioned co-monomers, in polymerized form, as well as initiator moieties and/or crosslinker moieties (to be extent initiators and/or crosslinking agents are used in the preparation of the dimethoxyphenol-based polymer and end up being incorporated into the dimethoxyphenol-based polymer as a result of the polymerization).

The term [meth]acrylates or [meth]acrylamides, as used herein, means the monomer can be either an acrylate or methacrylate or acrylamide or methacrylamide. Preferred co-monomers, in certain embodiments of the invention, include those capable of providing copolymers which are glassy materials at room temperature (e.g., styrene and methyl [meth]acrylate) and/or other monomers that can be derived from lignin or other biomass materials (e.g., vanillin [meth]acrylate and other guaiacol [meth]acrylates).

The dimethoxyphenol-based polymer may also be grafted to or grafted from particles, nanoparticles, and/or surfaces including, but not limited to, linoleum, granite, gold, concrete, silica, silicon dioxide, poly(dimethylsiloxane), poly (norbornene)s, poly(carbonate)s, graphene, graphite, diamond, garnet, ruby, emerald, topaz, talc, glass, zinc, steel, asphalt, ceramics, porcelain, tin, aluminum, foil, cloth, cotton, cellulosic fibers, lignin fibers, tetrafluoroethylene polymers, polyimides, quartz, nylon, silk, rayon, carbon nanotubes, nanowires, clay, and other organic or inorganic surfaces of varying roughness, flexibility, strength, and size.

The dimethoxyphenol-based polymer may also be a bulk or composite material. Many different nanoparticles and nanofibers may be blended into a dimethoxyphenol-based polymer before, during or after polymerization to impart different or enhanced properties to the product material. Nanoparticles and nanofibers of any of the above-mentioned types of materials or substances may be utilized as media from which, or to which, a dimethoxyphenol-based polymer may be synthesized or attached/grafted.

Possible applications for the dimethoxyphenol-based monomers and polymers of the present invention are numerous, as they can be used as modifiers for nearly any other existing plastic or composite material. Such uses and potential applications include, but are not limited to, cosmetics, personal health and beauty, food storage and processing, pharmaceuticals, energy transportation and storage, water purification, insulation, automotive parts, windows, housing, water treatment, paper-making, waste treatment, recycling, containers, membranes, battery and fuel-cell parts, aircraft equipment and parts, medical device coatings, sterile medical equipment casing, skin grafts, clothing, inks, resins for 3D (or normal) printing, viscosity controllers, food additives, preservatives, antioxidants, packaging, glasses, bottles, cups (disposable, washable, and/or reusable plastics), cutlery, optical coatings, electronics casings, sporting equipment, shoes, fasteners (zip-ties, buttons, tacks), paint, car paint, decorations, linoleum, counter tops, kitchen appliances, dampeners, carbonator coatings, gas-tank liners, toys, building blocks, microwave-safe or oven-safe containers and cookware, writing utensils, gaskets, gears, carpets, paneling, flooring, wood alternatives, carpentry equipment, grinders, razors, solar devices, glasses coatings, glasses frames, lenses, compact discs, lithographic masks, self-healing materials, rocket parts, space vehicle or interstellar vehicle parts, UV insulators, radiation shielding, satellite parts, impact-resistance coatings, bullet-proof vests and windows, space suit masks, robot parts, prosthetics, contact lenses, structural elements and binders in buildings, camera parts, cuvettes, mosquito nets, fishing line and nets, boat parts and coatings, implants, coatings for wearable electronics, high-temperature resins, Kevlar® polyimide alternatives, surfactants, lubricants, faux leather and fabric, firefighter protective equipment, cookware coatings, corrosion-resistant coatings, pipes, manifolds, medical instruments and instrument trays, electrical connectors, sensors, analytical instrument parts, semiconductor wafer handling components, components and seals for pumps, components and seals for compressors, bearings, bushings, cleaning pads, heat shields, engine components and seals, hoses, engine housing, valves, solenoids, latexes, nylons, aerospace parts, chemical processing and transportation devices, subterranean vehicles, [deep-sea] submersibles, naval equipment, bullet or missile casings, weaponry and ammo, firearms, hunting equipment, archery equipment, musical equipment, guitar strings and cases, seals, caulks, benches and seating, furniture and furniture coatings, tables, vibration dampeners, expansion joints, o-rings, custom-shaped parts, stock rods and sheets, emergency responder kits, flame-retardant coatings, snow-mobiles, skis, snowboards, snow-shoes, winter-wear, umbrella parts, rain jackets, protective clothing, masks, rollerblade or roller-skate parts, bicycle parts, wear-resistant coatings, color binders, street signs, vehicle bumpers, fluid-handling parts, sidewalks, driveways, pavement, alternatives for ceramics, train parts, anti-static coating, substrates for circuitry, pads, stoppers, vacuum and vacuum-cleaner parts, wire and cable tapes, pressure-sensitive adhesives, transformer and capacitor parts and insulation, shims, machinable parts, business equipment, nets, sockets, contractors, heat deflectors, radiation filters or dampeners, moisture-resistant coatings, wind turbine blades and parts, containers for nuclear waste storage and transportation, rollers, pressure discs, pistons, filler materials, connectors, medical tubing, syringes, catheter parts, pace-makers, implantable devices, belting, mesh, filters, sutures, medical leads, window coverings (e.g., drapes and blinds), brushes, bridge parts, cords, cables, liners, bags, pottery, washer and dryer parts, dishwasher parts, saw blades, sanders, brakes, stovetops, countertops, flooring, shingles, and polar exploration equipment.

Applications that are likely to benefit the most from dimethoxyphenol-based monomers and polymers in accordance with the present invention are those that require stability at temperatures near or above 100° C.; corrosion, solvent and/or abrasion resistance; high strengths; and optical characteristics (such as clarity). However, the dimethoxyphenol-based monomers are also useful for modulating/enhancing properties of materials at use temperatures below 100° C. The monomers and polymers are especially suitable for use in the aerospace, business, machining, transportation, chemical, construction, emergency-response, defense, consumer products, and medical industries. For example, medical equipment or devices often need to be sterilized at high temperatures and extreme pressures, so a strong polymer is desirable that will not warp under extreme conditions. Deep-sea or space explorers, emergency responders, and soldiers may encounter similarly harsh environments, so their vessels, protective gear, and equipment all must be reliable, protective, and preferably light-weight (all characteristics available through the incorporation of dimethoxyphenol-based monomers into polymers). The high $T_g$'s of polymers produced from these monomers also make the polymers suitable for replacing metal components in a number of machine parts, such as in engines. The transportation industry needs light-weight and high-$T_g$ materials, such as the dimethoxyphenol-based plastics of the present invention, to reduce the fuel load. Aerospace applications and space suits also require light-weight, strong, impact- or abrasion-resistant, and heat- and/or radiation-resistant/shielding materials to withstand impact from space debris and landing, harsh conditions of extraterrestrial terrains, high temperatures from re-entry, radiation from the sun, and so on; dimethoxyphenol-based monomers are capable of imparting these characteristics into materials already use by the aerospace industry as well as new plastics. The solvent resistance of the dimethoxyphenol-based monomers, when polymerized, can also benefit the chemical and nuclear industries, as coatings and plastics comprised of such monomers may eliminate or reduce corrosion of related equipment, piping, reactors, and storage tanks.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Synthesis and Purification of Syringyl Methacrylate

Syringol (99%, Fisher Scientific, used as received) was acylated with 1.02 molar equivalents of methacrylic anhydride (94%, inhibited with 2000 ppm Topanol® A, Sigma-Aldrich, used as received) using catalytic amounts of 4-dimethylaminopyridine (DMAP, >99%, Sigma-Aldrich, recrystallized from toluene), a reaction temperature of 60° C., and reaction times between 24 h and 72 h. Syringol-to-Syringol Methacrylate conversions of >60 mol-% were achieved at higher DMAP contents (i.e., 0.06 mol/mol DMAP/methacrylic anhydride). After washing the syringyl methacrylate product in dichloromethane with a saturated sodium bicarbonate solution, 1.0 M NaOH, 0.5 M NaOH, 1.0 M HCl, and deionized water and then concentrating the product by rotary evaporation, the syringyl methacrylate was fractionated to high purity using a heat-decant-cool cycle in either hexanes or petroleum ether. The monomer/hydrocarbon mixture was heated to reflux while stirring and subsequently decanted into a new flask, partially separating the syringyl methacrylate from insoluble viscous orange byproducts. Upon cooling, syringyl methacrylate phase-separated from the supernatant. This procedure was repeated with the syringyl methacrylate/hexanes (or petroleum ether) mixture until the phase-separating syringyl methacrylate layer vitrified at room temperature, at which point the product was collected by Buchner filtration (7 wt-% yield, >98 mol-% purity or >99 mol-% if recrystallized once more from ethanol). Alternatively, the washed and concentrated syringyl methacrylate was purified by automated column chromatography (Silica gel, stepped elution of 1:9 [3 column volumes] to 2:8 [8 column volumes] v/v ethyl acetate in hexanes, >98 mol-% purity) and then recrystallized once from ethanol (>99 mol-% purity). The identity of the product as syringyl methacrylate was confirmed by $^1$H NMR: $^1$H NMR δ ppm (CDCl$_3$, 600 MHz): 7.14 (1H, dd, J=12 Hz, 12 Hz), 6.63 (2H, d, J=12 Hz), 6.40 (1H, q, J=1.2 Hz), 5.76 (1H, q, J=1.5 Hz), 3.82 (6H, s), 2.09 (3H, dd, J=1.2 Hz, 1.4 Hz).

Synthesis and Characterization of Poly(syringyl methacrylate) and Heteropolymers Containing Syringyl Methacrylate Polymers were synthesized and purified following the procedures described in Holmberg et al., "A Facile Method for Generating Designer Block Copolymers from Functionalized Lignin Model Compounds." ACS Sustainable Chem. Eng. 2014, 2(4), 569-573 and Holmberg et al., "RAFT Polymerization and Associated Reactivity Ratios of Methacrylate-Functionalized Mixed Bio-oil Constituents. Polym. Chem. 2015, 6(31), 5728-5739. 2-Cyano-2-propyl benzodithioate (CPB) was used as the chain transfer agent and 2,2'-azobisisobuyronitrile (AIBN) was used as the free radical initiator. The components of the heteropolymers included one or more of the following in addition to syringyl methacrylate (SM): 4-ethylguaiacyl methacrylate (EM, 4-ethyl-2-methoxyphenyl methacrylate), vanillin methacrylate (VM, 4-formyl-2-methoxyphenyl methacrylate), and/or creosyl methacrylate (CM, 4-methyl-2-methoxyphenyl methacrylate).

Reaction conditions and size-exclusion chromatography (SEC) data for the homopolymers and heteropolymers are reported in Table S1. Note: macromolecular characterization equipment details are provided as footnotes to the table. Monomer compositions, monomer-to-polymer conversions (x), and cumulative polymer compositions were determined using a method described in the literature (Holmberg et al., RAFT Polymerization and Associated Reactivity Ratios of Methacrylate-Functionalized Mixed Bio-Oil Constituents. Polym. Chem. 2015, 6(31), 5728-5739), the vinyl peaks for SM listed above (6.40 ppm and 5.76 ppm), and the polymer peaks (fit using MestReNova Software) indicated below. Spectra were analyzed in triplicate to determine the 95% confidence in the composition, conversion, and tacticity measurements.

Poly(syringyl methacrylate) [PSM]: NMR δ ppm (CDCl$_3$, 600 MHz): 7.18-6.79 (1H, br), 6.67-6.14 (2H, br), 3.94-3.30 (6H, br), 3.30-1.35 (5H, many br). Non-ambient temperature (58° C.) $^1$H NMR data (CDCl$_3$ with 5 wt-% trifluoroacetic anhydride, 400 MHz) were utilized for tacticity estimates. The α-methyl protons (1.90-1.45 ppm) were split into broad peaks representative of triads with approximate chemical shifts of 1.76 ppm (mm), 1.69 (mr and rm), and 1.64 ppm (rr), which were used to estimate tacticity. These triad peaks were assumed to be located in the same order as the analogous triad protons in poly (methyl methacrylate) and poly(phenyl methacrylate), in which mm is further downfield and rr is further upfield relative to the single mr/rm peak. The fractions of racemo diads ($f_r$) of 0.90±0.05 and syndiotactic triads ($f_{rr}$) of 0.85±0.09 for PSM-21 are greater than the f of ~0.75 (and $f_r$ of ~0.60) reported for the softwood polymers (Holmberg et al., Softwood Lignin-Based Methacrylate Polymers with Tunable Thermal and Viscoelastic Properties. Macromolecules 2016, 49(4), 1286-1295), which are considered atactic.

Poly(4-ethylguaiacyl methacrylate-co-syringyl methacrylate) [P(ES)]: $^1$H NMR δ ppm (CDCl$_3$, 600 MHz): 7.15-6.79 (1H/EM+1H/SM, br), 6.79-6.24 (2H/EM+2H/SM, 3 br), 3.94-3.30 (3H/EM+6H/SM, br), 3.30-1.24 (5H/EM+5H/SM, many br), 1.24-1.00 (3H/EM, br). Polymer composition was determined via the characteristic EM peak at 1.24-1.00 ppm. The area of the peak was referenced to the area of the aromatic proton peaks (7.15-6.79 ppm and 6.79-6.24 ppm) and the methoxy proton peak (3.94-3.30 ppm) to estimate error. Monomer feed composition (mol/mol): $f_{EM}$ =0.951±0.003, $f_{SM}$=0.049±0.003. Polymer composition (mol/mol): $F_{EM}$=0.95±0.02, $F_{SM}$=0.05±0.02.

Poly(creosyl methacrylate-co-4-ethylguaiacyl methacrylate-co-syringyl methacrylate) [P(CES)]: $^1$H NMR δ ppm (CDCl$_3$, 600 MHz): 7.15-6.81 (1H/CM+1H/EM+1H/SM, br), 6.81-6.52 (2H/CM+2H/EM, 2 br), 6.52-6.30 (2H/SM, br), 3.87-3.30 (3H/CM+3H/EM+6H/SM, br), 3.30-1.27 (5H/CM+5H/EM+5H/SM, many br), 1.24-1.00 (3H/EM, br). Polymer composition was determined using the characteristic EM peak at 1.24-1.00 ppm and the characteristic SM peak at 6.52-6.30 ppm. The areas of these peaks were referenced to the area of the aromatic proton peaks (7.15-6.81 ppm and 6.81-6.30 ppm) and the methoxy proton peak (3.87-3.30 ppm) to estimate error. Monomer feed composition (mol/mol): $f_{CM}$=0.191±0.003, $f_{EM}$=0.339±0.004, $f_{SM}$=0.469±0.004. Polymer composition (mol/mol): $F_{CM}$=0.16±0.03, $F_{EM}$=0.36±0.03, $F_{SM}$=0.48±0.02.

Poly(vanillin methacrylate-co-4-ethylguaiacyl methacrylate-co-syringyl methacrylate) [P(VES)]: $^1$H NMR δ ppm (CDCl$_3$, 600 MHz): 9.94-9.44 (1H/VM, br), 7.45-7.18 (3H/VM, br), 7.18-6.79 (1H/EM+1H/SM, br), 6.75-6.30 (2H/EM+2H/SM, 2 br), 3.82-3.30 (3H/VM+3H/EM+6H/SM, br), 3.30-1.24 (5H/VM+5H/EM+5H/SM, many br), 1.24-1.00 (3H/EM, br). Polymer composition was determined using the characteristic EM peak at 1.24-1.00 ppm and the characteristic VM peaks at 9.94-9.44 ppm and 7.45-7.18 ppm. The areas of these peaks were referenced to the area of the aromatic proton peaks (7.48-6.30 ppm) and the methoxy proton peak (3.82-3.30 ppm) to estimate error. Monomer feed composition (mol/mol): $f_{VM}$=0.226±0.007, $f_{EM}$=0.227±0.003, $f_{SM}$=0.548±0.007. Polymer composition (mol/mol): $F_{VM}$=0.24±0.02, $F_{EM}$=0.23±0.01, $F_{SM}$=0.53±0.02.

TABLE S1

Polymerization conditions[a] and characteristics of polymers containing SM segments

| | $[M]_0/[C]_0$[b] (mol/mol) | $[M]_0/[S]$[b] (wt/wt) | t (h) | x (mol/mol) | $M_{n,calc}$[c] (kDa) | $M_{n,RI}$[d] (kDa) | $M_{n,LS}$, $M_{w,LS}$[e] (kDa) | Đ[d,f] | $T_g$ (° C.) |
|---|---|---|---|---|---|---|---|---|---|
| PSM-24 | 219 | 0.94 | 3.3[g] | 0.53 | 29 | 24 | — | 1.74 | 205 |
| PSM-21 | 137 | 0.94 | 6.5 | 0.87 | 25 | 21 | — | 1.51 | 203 |
| PSM-11 | 83 | 0.50 | 5.0 | 0.50 | 11 | 11 | — | 1.62 | 185 |
| PSM-A[h,i] | 285 | 0.96 | 0.3[g] | 0.53 | 37 | 38 | — | 1.61 | — |
| PSM-B[h] | 229 | 0.53 | 1.5 | 0.33 | 22 | 20 | — | 1.73 | — |
| PSM-C | 120 | 0.92[j] | 2.8 | 0.56 | 16 | 17 | — | 1.61 | — |
| PSM-D | 131 | 0.52[j] | 9.0 | 0.86 | 23 | 21 | — | 1.47 | — |
| P(VES) | 229 | 0.94 | 5.5 | 0.82 | 39 | 36 | 35, 52 | 1.45 (1.50[e]) | 159 |

TABLE S1-continued

Polymerization conditions[a] and characteristics of polymers containing SM segments

|  | $[M]_0/[C]_0$[b] (mol/mol) | $[M]_0/[S]$[b] (wt/wt) | t (h) | x (mol/mol) | $M_{n,calc}$[c] (kDa) | $M_{n,RI}$[d] (kDa) | $M_{n,LS}, M_{w,LS}$[e] (kDa) | Đ[d,f] | $T_g$ (°C.) |
|---|---|---|---|---|---|---|---|---|---|
| P(CES) | 231 | 0.94 | 5.5 | 0.78 | 37 | 32 | 35, 47 | 1.38 (1.32[e]) | 154 |
| P(ES) | 231 | 0.94 | 5.5 | 0.76 | 36 | 33 | 36, 46 | 1.32 (1.30[e]) | 114 |

[a]The homopolymers labeled by numbers and heteropolymers were synthesized at 72° C. in anisole with 5 wt-% N,N-dimethylformamide as an internal standard and with an initiator (I, 2,2'-azobisisobutyronitrile [AIBN]) to chain-transfer agent (C, 2-cyano-2-propylbenzodithioate) ratio of 0.155 ± 0.005 mol/mol. Polymers labeled by letters deviated from this procedure as indicated via superscripts h, i, and j.
[b]Abbreviations stand for monomer (M) and solvent (S).
[c]See below for equation.
[d]Determined relative to polystyrene standards using data from SEC with refractive-index (RI) detectors and a chloroform eluent.
[e]Determined by Zimm analysis using data from SEC with a tetrahydrofuran (THF) eluent and light-scattering (LS) detectors.
[f]For comparison, a PSM prepared by free-radical polymerization had a Đ of 2.65, and PSMs prepared with an ineffective chain-transfer agent had Đ's of 2.14 and 2.39.
[g]Reaction vitrified.
[h]Reaction temperature was 90° C.
[i]$[I]_0/[C]_0 = 0.32 \pm 0.05$ mol/mol.
[j]Solvent was chlorobenzene.

$$M_{n,calc} = \frac{[M]_0 \cdot x \cdot M_{monomer}}{[C]_0 \cdot (1-(1-x)^{C_{tr,app}}) + d \cdot f \cdot [I]_0 \cdot (1-e^{-k_d \cdot t})} + M_C \quad (S1)$$

$M_{monomer}$ (compositional average of the monomer molecular weights)=
222 g/mol for PSM syntheses
221 g/mol for P(VES) synthesis
219 g/mol for P(CES) synthesis
220 g/mol for P(ES) synthesis
$M_C$ (molecular weight of C)=221 g/mol.
f (Initiation efficiency of I)=0.5 (Moad et al. "Living Radical Polymerization by the RAFT Process." Aust. J. Chem. 2005, 58(6), 379-410).
$k_d$ (decomposition rate of I)≈$5.7\times10^{-5}$ s$^{-1}$ at 72° C. or $5.4\times10^{-4}$ s$^{-1}$ at 90° C. (AkzoNobel Product Data Sheet: Perkadox® AIBN. AkzoNobel PolymerChemistry: Amersfoort, The Netherlands, 2015).
d (number of chains produced in a methyl methacrylate-like radical-radical termination event)=1.67 (Moad et al. "Living Radical Polymerization by the RAFT Process." Aust. J. Chem. 2005, 58(6), 379-410).
$C_{tr,app}$ (apparent chain-transfer coefficient) was approximately 2.6 for hardwood and softwood monomers polymerized under the reaction conditions described herein. $C_{tr,app}$ was assumed to be approximately 2.6 for reactions performed under different conditions (the PSMs labeled by letters, which either had S=chlorobenzene or a reaction temperature of 90° C.), noting that this factor affects $M_{n,calc}$ by <1% for PSM-C and PSM-D but could cause $M_{n,calc}$ to be overestimated by up to 14% for PSM-A, 34% for PSM-B, and 11% for PSM-C.

Equation S1 accounts for chains initiated by free radicals and the approximate time-dependent consumption of chain-transfer agent. The corresponding equation for the maximum number-average degree of polymerization ($X_{n,max}$) assumes 100% consumption of the chain-transfer agent at all conversions, no chains initiated by free radicals, and no contribution of $M_C$.

Equipment $^1$H NMR data were collected and analyzed following a previously reported methodology (Holmberg et al., Softwood Lignin-Based Methacrylate Polymers with Tunable Thermal and Viscoelastic Properties. Macromolecules 2016, 49(4), 1286-1295). SEC data for the PSM homopolymers and heteropolymers (relative to polystyrene standards) were determined on an Agilent HP 1100 instrument with chloroform as the eluent (1.0 mL/min, HP 1047A RI Detector, Carian PLgel Mixed-C columns in series). Additional SEC data with light-scattering were determined for the heteropolymers using a Viscotek VE 3580 instrument with tetrahydrofuran (THF) as the eluent (1.0 mL/min; Viscotek VE3580 RI, UV-PDA, and Viscotek 270 Dual detectors; Waters Styragel HR1 and HR4 columns [7.8×300 mm] in series). Analogous light-scattering SEC experiments were not performed on the PSM homopolymers due to their poor solubility in THF.

Thermogravimetric analysis (TGA, 10° C./min under airflow), differential scanning calorimetry (DSC, 5° C./min under air), and dynamic mechanical analysis (DMA) data were collected and analyzed as described in the literature (Holmberg et al., Softwood Lignin-Based Methacrylate Polymers with Tunable Thermal and Viscoelastic Properties. Macromolecules 2016, 49(4), 1286-1295) to facilitate comparisons to softwood lignin-based polymers, but with minor differences indicated as follows. Temperature windows for DSC analysis [40-180° C. for PEM; 60-180° C. for P(ES); 60-190° C. for P(CES) and P(VES); and 140-240° C. for PSM] were chosen to minimize end-group thermolysis while also generating an above-$T_g$ baseline of at least 20° C. to facilitate analysis. Samples for DMA (0.3 mm in thickness, 8 mm in diameter) were prepared by pressing polymer powder at high temperature [150° C. for P(ES); 190° C. for P(CES) and P(VES); and 240° C. for PSM-21] and pressure (1 metric ton) for 15 min. Frequency sweeps were taken at 10° C. temperature intervals, beginning near the $T_g$ and ending either when the polymer flowed out from between the parallel plates or slightly below the thermal degradation onset. Temperature sweeps were taken at 3° C./min at a frequency of 6.28 rad/s. Strain amplitudes [frequency sweep: 0.1-5% for P(ES), 0.06-5% for P(CES), 0.1-5% for P(VES), and 0.2-1% for PSM-21; temperature sweep: 0.05-5% for P(ES), 0.04-5% for P(CES), 0.06-5% for P(VES), and 0.1-1.5% for PSM-21] were varied to keep within the linear regime. Data were shifted to a reference temperature of 180° C. (the maximum temperature before polymer flow) for P(ES) and 220° C. (the only overlapping temperature) for all other macromolecules using time-temperature superposition.

Table S2 shows selected characteristics of the syringyl methacrylate-containing heteropolymers.

TABLE S2

Selected characteristics of SM-containing
heteropolymers to facilitate comparison[a]

|  | P(ES) | P(CES) | P(VES) |
|---|---|---|---|
| $k_{p,app}$[b] (h$^{-1}$) | 0.23 ± 0.01 | 0.26 ± 0.02 | 0.26 ± 0.02 |
| $C_{tr,app}$[c] | 3.0 ± 0.3 | 2.5 ± 0.3 | 2.3 ± 0.7 |
| $T_{g,calc}$[d] (° C.) | 114 ± 3 | 153 ± 3 | 162 ± 3 |
| $T_{g,meas}$[e] (° C.) | 114 ± 1 | 154 ± 1 | 159 ± 1 |
| $T_o$[f] (° C.) | 256 ± 5 | 264 ± 5 | 260 ± 5 |
| $\eta_0$[g] (kPa · s) | 0.2[h] | 37 | 39 |

[a]Values reported with 95% confidence intervals if available.
[b]Apparent propagation rate normalized to an initiator-to-chain-transfer ratio of 0.100.
[c]Apparent chain-transfer coefficient determined using the Mayo equation and the change in dispersity at low conversions.
[d]$T_g$ calculated using the Fox equation and $T_g$'s of similar molecular weight homopolymers (130° C. for PVM, 110° C. for PEM, 126° C. for PCM, and 205° C. for PSM).[8]
[e]Average $T_g$ from the midpoint of the inflection in the second and third heat of the DSC data (5° C./min).
[f]Onset degradation temperature determined in air using TGA (10° C./min).
[g]Zero-shear viscosity at 220° C. determined by the Cox-Merz rule.
[h]Value extrapolated from data collected at 160-180° C. assuming Arrhenius behavior.

The polymerization rate and reactivity of syringyl methacrylate were found to be consistent with the polymerization rates and reactivities of softwood lignin-based monomers (EM, CM, VM and guaiacyl methacrylate (CM), despite the presence of a second methoxy group ortho to the methacrylate substituent in syringyl methacrylate (SM). $k_{p,app}$'s were determined to be the same at 95% confidence regardless of SM content and compare favorably to the $k_{p,app}$'s reported for the softwood lignin-based monomers (see Table S2). The compositions of the monomer mixtures and the cumulative compositions of the heteropolymer changes also do not change measurably with respect to conversion [x], further indicating the similar reactivities of the hardwood and softwood lignin-based monomers and the likely random distributions of monomer segments in each chain. Consequently, syringol and guaiacol contents in a mixture can be manipulated without harming the predictability of conversions, monomer distributions and molecular weight.

Control over the RAFT polymerizations also is consistent between guaiacylic and syringylic monomers, simplifying the process of tailoring macromolecular characteristics. First, the dispersities decrease with respect to increasing monomer conversion [x] and the normalized degrees of polymerization ($X_n/X_{n,max}$'s) change linearly with x, indicating that the polymerizations are controlled. Second, the size-exclusion chromatography (SEC) data are unimodal and the dispersities (also referred to as polydispersities) of the homopolymers and heteropolymers (1.32-1.74) are similar to or better (lower) than what has been previously reported for PVMs that were successfully chain-extended to generate self-assembling block copolymers. Finally, the dispersities and $X_n/X_{n,max}$'s for the homopolymers and heteropolymers change with respect to x in an approximately equivalent manner, albeit slightly shifted vertically due to differences in polymer solubility. The consistency of these data was confirmed by estimating the $C_{tr,app}$ from the heteropolymerizations using the Mayo equation. The resulting $C_{tr,app}$'s for the heteropolymers were within error of values reported for the polymerizations of GM, EM, CM, VM and corresponding mixtures. Additionally, $C_{tr,app}$ for SM homopolymerizations is approximately the same as for softwood lignin-based monomer polymerizations, further establishing that the presence of the second o-methoxy group in SM has a surprisingly negligible effect on its polymerization behavior.

PSM-24 has a larger dispersity in part because the reaction mixture gelled. The lower dispersities listed in Table S1 were achieved by diluting the reaction mixture, reducing the target molecular weight, changing the solvent and incorporating softwood lignin-based methacrylate monomers. All of these changes contribute to reductions in solution viscosity and thus polymer dispersity.

The measured $T_g$'s of the PSM homopolymers (185-205° C. depending on molecular weight, see also Table S1) are among the highest reported for amorphous, linear polymers with aliphatic backbones, even greater than the $T_g$'s reported for poly(2,6-dimethylphenyl methacrylate (189° C.) and poly(2,6-diisopropylphenyl methacrylate (198° C.). A PSM of infinite molecular weight could have a $T_g$ as high as about 220° C., assuming Flory-Fox behavior when fitting data from Table S1. The $T_g$ of PSM-24 is about 75° C. higher than that of PVM and about 95° C. higher than that of PEM at similar number average molecular weight.

Syringyl methacrylate segments also can be incorporated into polymers to make predictable changes to the $T_g$ based on composition and the Fox equation. The actual and calculated Fox-based $T_g$'s were found to agree closely. For example, incorporating 5 wt % of SM segments into PEM raises the $T_g$ by 4° C. (from 110° C. to 114° C.), the predicted increase. The heteropolymers with compositions that mimic possible fractions of bio-oil ($f_{SM}$=0.48-0.55) were found to have similarly predictable, yet high (154° C. and 159° C.) glass transition temperatures. Furthermore, the onset thermal degradation temperatures in air for PSM (303±5° C.) and the heteropolymers (256-260° C.) are about 100° C. greater than each of the measured $T_g$'s; thus, these polymers can be melt-processed without significant thermal degradation.

The $\eta_0$'s for SM-containing polymers were found to span about 5 orders of magnitude and to depend largely on the SM content. For example, the $\eta_0$ at 220° C. is 17,000 k.Pas for PSM and significantly less for the SM-containing heteropolymers listed in Table S2. This window of $\eta_0$'s is substantial in comparison to the approximately 2 orders of magnitude spanned by the complete range of guaiacylic methacrylate polymers and could be even wider if higher molecular weight polymers, relative to PSM-24, were examined. Thus the use of syringyl methacrylate as a monomer provides a much wider space over which processability and deformation resistance can be optimized.

In summary, no other system of biobased monomers allows polymer $T_g$'s from about 100° C. (ideal for thermoformable, yet boiling water-stable, plastics, such as cups) to about 200° C. (ideal for heat- and flow-resistant materials, such as asphalt binders) to be accessed as readily as the dimethoxyphenol-based monomers described herein. The measurable changes in $T_g$ and $\eta_0$ at low content of SM, and the wide-ranging thermomechanical properties attainable through the dimethoxyphenol-based polymers of the present invention confirm that such monomers (e.g., syringyl methacrylate) are powerful add-in monomers for adjusting material properties. The similar polymerization characteristics between the dimethoxyphenol-based monomers of the present invention and other types of lignin-based monomers (in particular, monomers derived from softwood lignin) also greatly simplify the task of predicting a priori the macromolecular characteristics and properties of any heteropolymer containing dimethoxyphenol and syringylic segments. Hence, syringyl methacrylate, as well as the other dimethoxyphenol-based monomers described herein, is a biobased monomer extraordinarily capable of significantly raising polymer $T_g$'s and deformation resistances at comparatively low levels in polymers.

The successful synthesis and isolation of syringol methacrylate was somewhat unexpected, mainly because syringol tends to favor conversion to stable phenoxy radicals and colored quinones. The discovery that syringyl methacrylate can be successfully polymerized using RAFT polymerization also was somewhat unexpected, in view of the presence of o-methoxy groups in the monomer. Other poly(phenyl methacrylate) derivatives with bulky o-groups can be challenging to synthesize due to low ceiling temperatures and polymer thermal stabilities.

The polymerization rate and reactivity of syringol methacrylate were found to be consistent with the polymerization rate and reactivity of monomers derived from softwood lignin (EM, CM, VM and guaiacyl methacrylate [GM]), despite the presence of a second o-methoxy group in the syringyl methacrylate. The $k_{p,app}$ values observed were the same at 95% confidence regardless of SM content and compare favorably to the $k_{p,app}$'s previously for softwood monomers. The compositions of the monomer mixtures and the cumulative compositions of the heteropolymer chains also do not change measurably with respect to conversion, further indicating the similar reactivities of the hardwood (syringol-based) and softwood monomers and the likely random distributions of monomer segments in each chain. Consequently, the relative content of dimethoxyphenol-based monomer and guaiacol-based monomer in a polymerization mixture can be manipulated without harming the predictability of conversions, monomer distributions and molecular weight.

What is claimed is:

1. A polymer comprising, in polymerized form, at least one polymerizable monomer comprised of a phenyl ring, two methoxy groups substituted on the phenyl ring, and at least one substituent on the phenyl ring comprised of at least one polymerizable functional group which is an ethylenically unsaturated functional group, wherein the ethylenically unsaturated functional group has been polymerized in the polymer, wherein the at least one polymerizable monomer has a structure corresponding to formula (I):

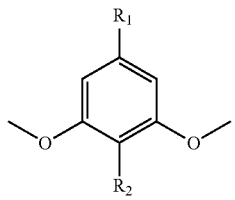

(I)

wherein R1 is a heteroatom-containing organic moiety selected from the group consisting of aldehyde-containing groups, ketone-containing groups, carboxylic acid-containing groups, and hydroxyl-containing groups; and wherein R2 is the substituent comprised of at least one polymerizable functional group which is an ethylenically unsaturated functional group.

2. The polymer of claim 1 additionally comprising, in polymerized form, one or more polymerizable co-monomers other than polymerizable monomers having structures corresponding to formula (I).

3. The polymer of claim 2, wherein the one or more polymerizable co-monomers are selected from the group consisting of lignin-based monomers, styrenes, phenyl [meth]acrylates, alkyl [meth]acrylates, [meth]acrylates other than alkyl [meth]acrylates and phenyl [meth]acrylates, terephthalates, amides, amines, diamides, diamines, dichlorides, nitriles, carboxylic acids, lactones, lactams, maleates, fumarates, malonates, maleinates, vinyls, vinyl esters, vinyl amides, [meth]acrylamides, thiols, dithiols, polythiols, enes, dienes, olefins, allyl monomers, azides, diazides, phosgene, carbonates, carbamates, succinates, alcohols, silanes, silicones, siloxanes, ethers, vinyl ethers, vinyl sulfides, isocyanates, epoxides, norbornenes, anhydrides, and combinations thereof.

4. The polymer of claim 2, wherein the polymer is a block copolymer, random copolymer, star polymer, brush polymer, or gradient copolymer.

5. A polymer comprising, in polymerized form, at least one polymerizable monomer comprised of a phenyl ring, two methoxy groups substituted on the phenyl ring, and at least one substituent on the phenyl ring comprised of at least one polymerizable functional group which is an ethylenically unsaturated functional group, wherein the ethylenically unsaturated functional group has been polymerized in the polymer, wherein the at least one polymerizable monomer has a structure corresponding to formula (I):

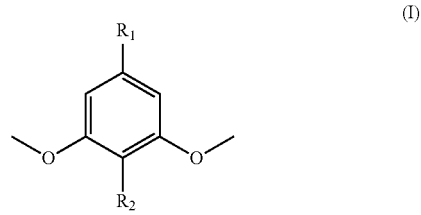

(I)

wherein $R_1$ is hydrogen or formyl and $R_2$ is [meth] acrylate.

6. The polymer of claim 5 additionally comprising, in polymerized form, one or more polymerizable co-monomers other than polymerizable monomers having structures corresponding to formula (I).

7. The polymer of claim 6, wherein the one or more polymerizable co-monomers are selected from the group consisting of lignin-based monomers, styrenes, phenyl [meth]acrylates, alkyl [meth]acrylates, [meth]acrylates other than alkyl [meth]acrylates and phenyl [meth]acrylates, terephthalates, amides, amines, diamides, diamines, dichlorides, nitriles, carboxylic acids, lactones, lactams, maleates, fumarates, malonates, maleinates, vinyls, vinyl esters, vinyl amides, [meth]acrylamides, thiols, dithiols, polythiols, enes, dienes, olefins, allyl monomers, azides, diazides, phosgene, carbonates, carbamates, succinates, alcohols, silanes, silicones, siloxanes, ethers, vinyl ethers, vinyl sulfides, isocyanates, epoxides, norbornenes, anhydrides, and combinations thereof.

8. The polymer of claim 6, wherein the polymer is a block copolymer, random copolymer, star polymer, brush polymer, or gradient copolymer.

* * * * *